(12) United States Patent
Predick et al.

(10) Patent No.: US 10,842,633 B2
(45) Date of Patent: Nov. 24, 2020

(54) SPINAL INTERBODY CAGE IMPLANT WITH FLEXIBLE BARBS

(71) Applicant: Life Spine, Inc., Huntley, IL (US)

(72) Inventors: Daniel P. Predick, West Lafayette, IN (US); Michael S. Butler, St. Charles, IL (US)

(73) Assignee: Life Spine, Inc., Huntley, IL (US)

( * ) Notice: Subject to any disclaimer, the term of this patent is extended or adjusted under 35 U.S.C. 154(b) by 204 days.

(21) Appl. No.: 15/439,702

(22) Filed: Feb. 22, 2017

(65) Prior Publication Data

US 2017/0239053 A1 Aug. 24, 2017

Related U.S. Application Data (60) Provisional application No. 62/298,534, filed on Feb. 23, 2016.

(51) Int. Cl.
*A61F 2/30* (2006.01)
*A61F 2/44* (2006.01)
(Continued)

(52) U.S. Cl.
CPC ........ *A61F 2/30749* (2013.01); *A61B 17/844* (2013.01); *A61B 17/864* (2013.01);
(Continued)

(58) Field of Classification Search
CPC .............. A61F 2/30749; A61F 2/30771; A61F 2/4455; A61F 2/447; A61F 2002/30131; A61F 2002/30472; A61F 2002/30774; A61F 2002/30787; A61F 2002/30904; A61F 2002/30354; A61F 2002/3038; A61F 2002/30382; A61F 2002/30794;
(Continued)

(56) References Cited

U.S. PATENT DOCUMENTS 8,313,528 B1 * 11/2012 Wensel ................... A61F 2/447
623/17.11
8,382,839 B1 * 2/2013 Wensel ............... A61F 2/30723
623/17.16

(Continued)

OTHER PUBLICATIONS

Search Report for International Application No. PCT/US2017/018989, dated Jun. 8, 2017, 10 pages.

*Primary Examiner* — Kevin T Truong
*Assistant Examiner* — Tracy L Kamikawa
(74) *Attorney, Agent, or Firm* — Foley & Lardner LLP (57) ABSTRACT

A spinal interbody cage implant includes a cage, an endplate, and flexible barbs. The endplate is separately attached to the cage and is configured to receive, hold and direct a flexible barb into an upper vertebral surface and a flexible barb into a lower adjacent vertebral surface. Each proximal leg of the cage is configured to receive the endplate, and has a lateral bore that receives a pin which retains the endplate. The endplate directs a first flexible barb upwardly toward an upper vertebral surface, and directs a second flexible barb downwardly toward a lower vertebral surface. Each flexible barb has a proximal head, a shaft extending from the head with a bore extending from the head to its distal end. Teeth are provided along the exterior surface of the shaft with two flats disposed on opposite sides thereof with a slit extending from the distal end towards the head.

21 Claims, 7 Drawing Sheets

(51) Int. Cl.
  *A61B 17/84*   (2006.01)
  *A61B 17/86*   (2006.01)
(52) U.S. Cl.
  CPC ...... *A61B 17/8625* (2013.01); *A61F 2/30771* (2013.01); *A61F 2/4455* (2013.01); *A61B 2017/8655* (2013.01); *A61F 2002/3079* (2013.01); *A61F 2002/30131* (2013.01); *A61F 2002/30331* (2013.01); *A61F 2002/30354* (2013.01); *A61F 2002/30433* (2013.01); *A61F 2002/30593* (2013.01); *A61F 2002/30774* (2013.01); *A61F 2002/30787* (2013.01); *A61F 2002/30841* (2013.01); *A61F 2002/30904* (2013.01)
(58) Field of Classification Search
  CPC ... A61F 2002/30841; A61F 2002/4475; A61B 17/844; A61B 17/8625; A61B 17/864; A61B 2017/8655
  See application file for complete search history.

(56) References Cited

U.S. PATENT DOCUMENTS

| | | | |
|---|---|---|---|
| 8,641,766 B2* | 2/2014 | Donner | A61B 17/70 623/17.16 |
| 2011/0230971 A1 | 9/2011 | Donner et al. | |
| 2012/0078373 A1* | 3/2012 | Gamache | A61B 17/8625 623/17.16 |
| 2013/0226300 A1 | 8/2013 | Chataigner et al. | |
| 2013/0268008 A1 | 10/2013 | McDonough et al. | |
| 2013/0317559 A1* | 11/2013 | Leavitt | A61B 17/1697 606/86 R |
| 2014/0180417 A1* | 6/2014 | Bergey | A61F 2/4455 623/17.16 |
| 2015/0202051 A1* | 7/2015 | Tanaka | A61F 2/4657 623/17.16 |
| 2016/0338849 A1* | 11/2016 | Ashleigh | A61F 2/447 |
| 2017/0007305 A1* | 1/2017 | Hollis | A61B 17/809 |

* cited by examiner

SPINAL INTERBODY CAGE IMPLANT WITH FLEXIBLE BARBS

CROSS-REFERENCE TO RELATED APPLICATIONS

This U.S. non-provisional patent application claims the benefit of and/or priority under 35 U.S.C. § 119(e) to U.S. provisional patent application Ser. No. 62/298,534 filed Feb. 23, 2016 titled "Spinal Interbody Cage Implant With Flexible Barbs," the entire contents of which is specifically incorporated herein by reference.

FIELD OF THE INVENTION

The present invention relates to orthopedic implants for the spine and, particularly, to interbody cages for spinal fusion.

BACKGROUND OF THE INVENTION

Many people contend with spine issues as a result of age, disease, and trauma, as well as congenital and acquired complications and conditions. While some of these issues can be alleviated without surgery, other issues respond better to surgery. In some cases, surgery may include placing an implant into the spine. If vertebral fusion is required, a spine implant known as an interbody cage along with bone graft or bone graft material may be used.

An interbody cage is a device that is placed in the disc space between adjacent vertebrae of a recipient's spine. The interbody cage includes openings, bores, and/or is porous or the like to permit the introduction and/or carrying of bone graft/bone graft material in order to allow the bone graft/bone graft material to grow from one vertebra through the interbody cage and into the adjacent vertebra. Such interbody cages provide excellent fixation such that most recipients do not require additional implants such as plates and/or bone screws.

It is desirable that the interbody cage utilize the subchondral bone at the end of the vertebra rather than reaming it away, as this can weaken the disc space and lead to postoperative subsidence of the interbody cage into the vertebrae, causing a loss of fixation. While there are various geometries of interbody cages, a rectangular geometry allows for more surface area between the cage and the cage endplate, which in turn decreases the force per unit area on the cage endplate. Current interbody cages often fail as a result of the endplate not being able to support the stress of the cage. Decreasing the force per unit area should lead to less endplate failures and cage subsidence.

However, while numerous interbody cages have been designed over the years, they are deficient in many respects. It is therefore an object of the present invention to provide an interbody cage that overcomes the deficiencies of the prior art.

SUMMARY OF THE INVENTION

A spinal interbody cage implant includes a cage, an endplate, and flexible barbs, spikes, or the like (collectively, "barbs"). The endplate is separately attached to the cage and is configured to receive, hold and direct a flexible barb into an upper vertebra and a flexible barb into a lower adjacent vertebra.

The cage is generally, but not necessarily, U-shaped having a distal cavity and, with attachment of the endplate, a proximal cavity. Upper and lower surfaces of the cage and endplate include serrations or the like that grip respective upper and lower vertebral surfaces.

The cage has a generally tapered distal end and two proximal legs. Each proximal leg is configured to receive the endplate and has a lateral bore that receives a pin which is received in and retains the endplate.

The endplate has distal sides that are configured for reception by the two configured proximal legs, a first bore extending from a front of the endplate and configured to direct a flexible barb upwardly toward an upper vertebral surface, and a second bore extending from the front of the endplate and configured to direct a flexible barb downwardly toward a lower vertebral surface.

Each flexible barb has a proximal head, a shaft extending from the head with a bore extending from the head to its distal end. Teeth or the like are provided along the exterior surface of the shaft with two flats disposed on opposite sides of the shaft along with a slit extending from the distal end towards the head. The head has internal threading that aids in inserting the barb into the cage during implantation.

The cage and endplate may be made from metal such as titanium, stainless steel or an alloy of either, PEEK, PET or PETE, carbon fiber, or other biocompatible material. The flexible barbs are formed of a flexible biocompatible material such as, but not limited to, PEEK, PET, PETE, or the like.

Further aspects of the present invention will become apparent from consideration of the drawings and the following description of a form of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The features of the invention will be better understood by reference to the accompanying drawings which illustrate various views of a form of the present invention, wherein.

DETAILED DESCRIPTION OF THE INVENTION

Figure 1:
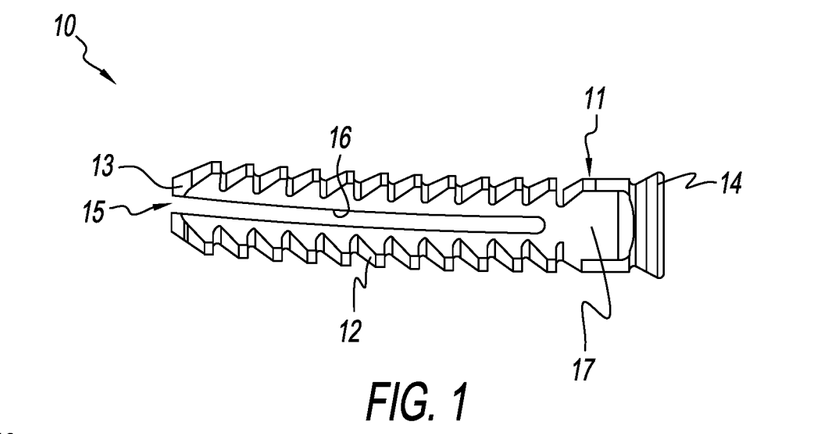
FIG. 1 is a side view of a flexible barb of the present spine interbody cage implant fashioned in accordance with the present principles.
Figures 2, 3:
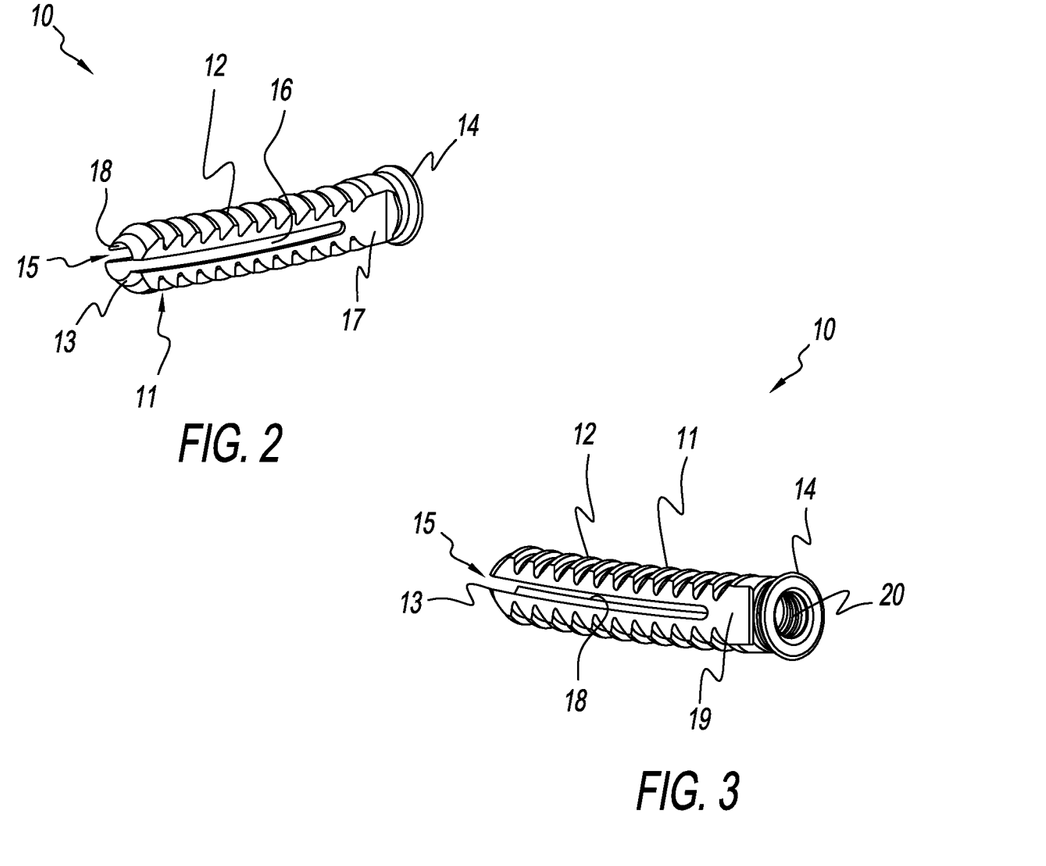
FIG. 2 is an isometric front side view of the flexible barb of FIG. 1.
FIG. 3 is an isometric rear side view of the flexible barb of FIG. 1.

FIGS. 1-3 show a barb, spike, or the like generally designated 10 (collectively, barb 10) that is one component or element of an interbody cage implant 100 (see FIGS. 9 and 10) that is used for the spine and, particularly, in the disc space of adjacent vertebrae of the spine in order to provide and/or promote fusion thereof. The barb 10 is formed of a flexible biocompatible material and is characterized by a generally elongated shaft 11 having a having a head 14 at a proximal end thereof, and a tip 13 at a distal end thereof. The head 14 has an internally threaded socket 20 that allows threaded engagement with a like threaded tool (not shown) for insertion of the barb 10.

The shaft 11 has external serrations 12 that extend from the tip 13 to the head 14. As best seen in FIG. 1, the serrations 12 are step-shaped relative to the tip 13 to allow insertion of the barb but prevent the barb from backing out. Other styles of serrations or teeth, however, may be used. A bore 15 extends from the tip 13 to the socket 20 thereby making the barb also a cannula. As seen in FIG. 2, one side of the shaft 11 has a flat 17 that extends from the tip 13 to the head 14. As seen in FIG. 3, another side of the shaft 11 also has a flat 19 that extends from the tip 13 to the head 14. The flats 17 and 19 are preferably, but not necessarily, opposite one another on the shaft 11. A slot, channel or the like 16 is provided along the flat 17 that extends from the tip 13 to proximate the head 20. A slot, channel or the like 18 is likewise provided along the flat 19 that extends from the tip 13 to proximate the head 20. These characteristics of the barb 10 allow the barb to flex without compromising its integrity.

Figure 4:
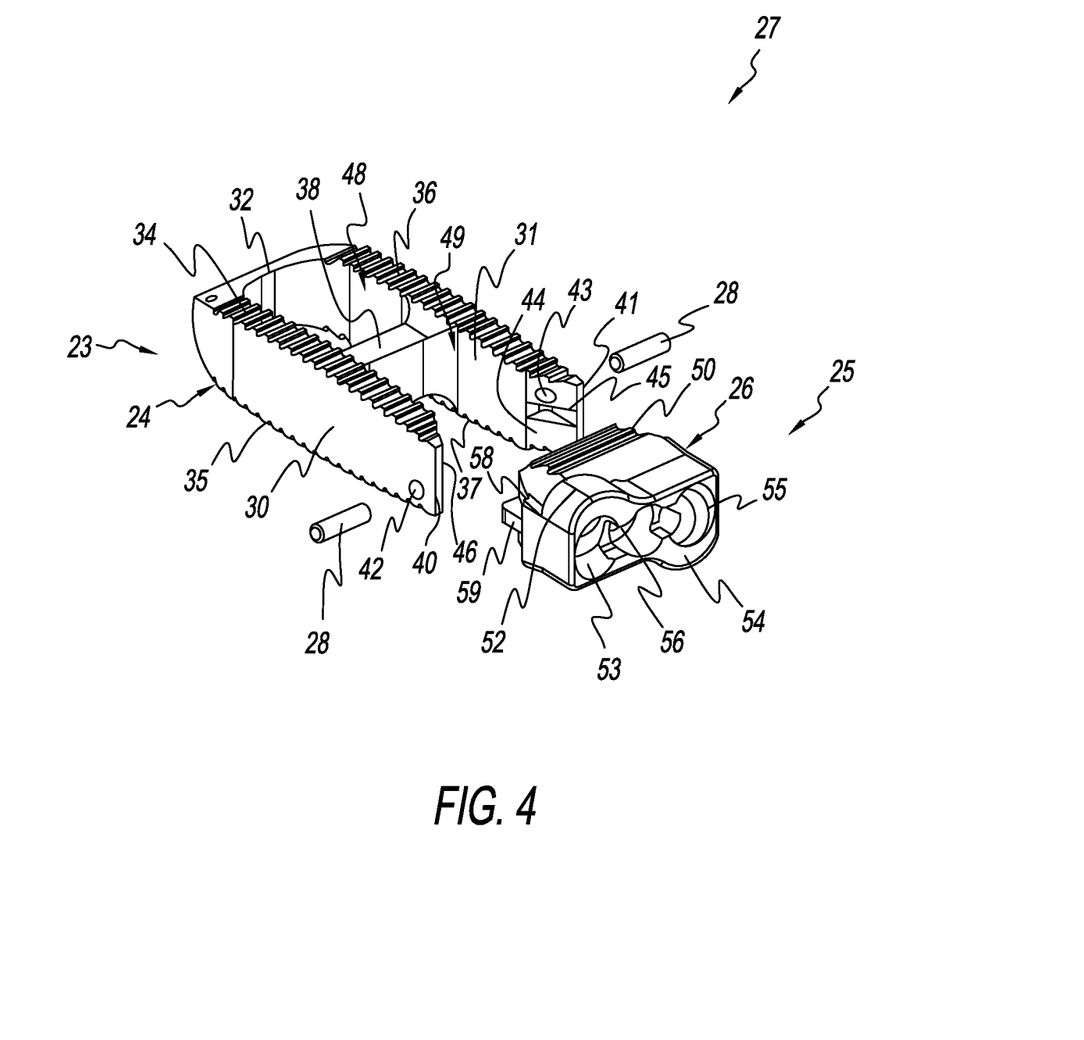
FIG. 4 is an isometric rear side exploded view of a cage and endplate of the present interbody cage implant.
Figure 5:
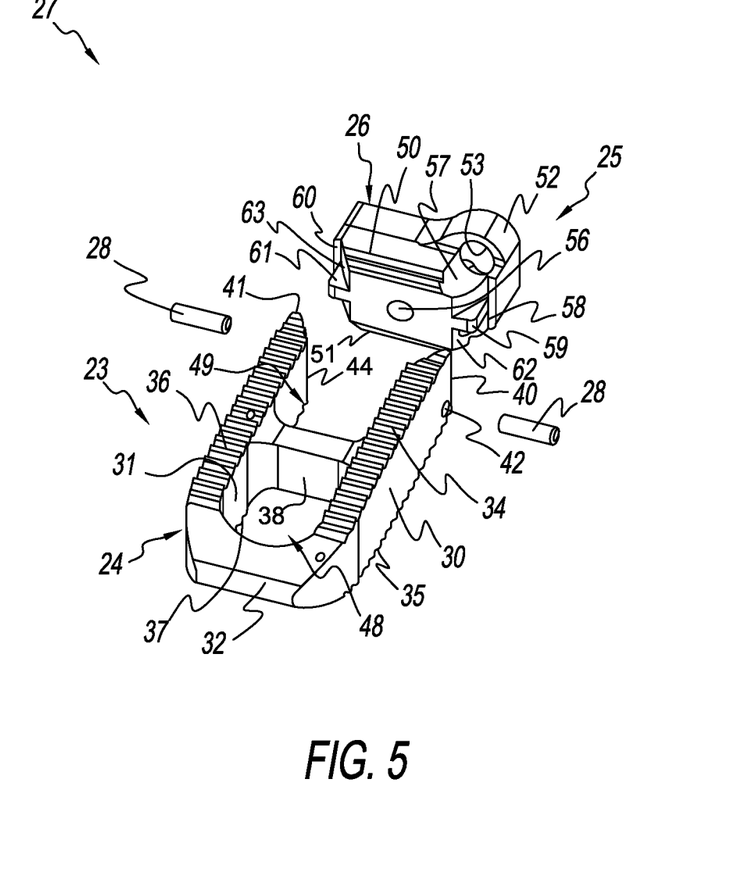
FIG. 5 is an isometric front top exploded view of the cage and endplate of the present interbody cage implant.

FIGS. 4 and 5 show an interbody cage assembly 27 in an exploded view that is defined by a cage 23 and an endplate 25. The cage 23 has a generally U-shaped (but may be different if desired) body 24 having an angled, beveled, or tapered distal end 32, a first leg 30 extending from a first side of the end 32, and a second leg 31 extending from a second side of the end 32, the nomenclature first and second being arbitrary. The first and second legs 30, 31 are spaced to receive the endplate 25. A spur or the like 38 extends between the first and second legs 30, 31 to define a cavity 48 between the end 32 and the spur 38. Serrations, teeth or the like (collectively, serrations) 34 are provided along an upper (superior) side of the first leg 30, the serrations 34 providing gripping against a lower (inferior) surface of an upper vertebral surface (not shown) when implanted. Serrations, teeth or the like (collectively, serrations) 35 are likewise provided along a lower (inferior) side of the first leg 30, the serrations 35 providing gripping against an upper (superior) surface of a lower vertebral surface (not shown) when implanted. Serrations, teeth or the like (collectively, serrations) 36 are provided along an upper (superior) side of the second leg 31, the serrations 35 providing gripping against a lower (inferior) surface of an upper vertebral surface (not shown) when implanted. Serrations, teeth or the like (collectively, serrations) 37 are likewise provided along a lower (inferior) side of the second leg 31, the serrations 37 providing gripping against an upper (superior) surface of a lower vertebral surface (not shown) when implanted.

A proximal end 40 of the first leg 30 terminates in an angle, slant or taper 46 and includes a bore 42 that extends from a lower portion of the outside surface thereof to a lower portion of the inside surface thereof. A proximal end 41 of the second leg 31 also terminates in an angle, slant or taper 44 and includes a bore 43 that extends from an upper portion of the outside surface thereof to an upper portion of the inside surface thereof. Each bore 42, 43 is sized to receive a pin or the like 28. The pins 28 retain the endplate 25 onto the first and second ends 40, 41 of the cage body 24 as explained below.

The inside of the angle 44 of the end 41 of the second leg 31 is configured to receive and retain the endplate 25 and, particularly, a side of the endplate 25 as described below. As best seen in FIG. 4, the angle 44 has a slot 45 that extends the length of the angle 44 and cuts into the end 41 a depth towards the distal end 32. While not seen, the inside of the angle 46 of the end 40 of the first leg 30 has the same configuration as the inside of the angle 44 of the end 41 of the second leg 31.

Figure 9:
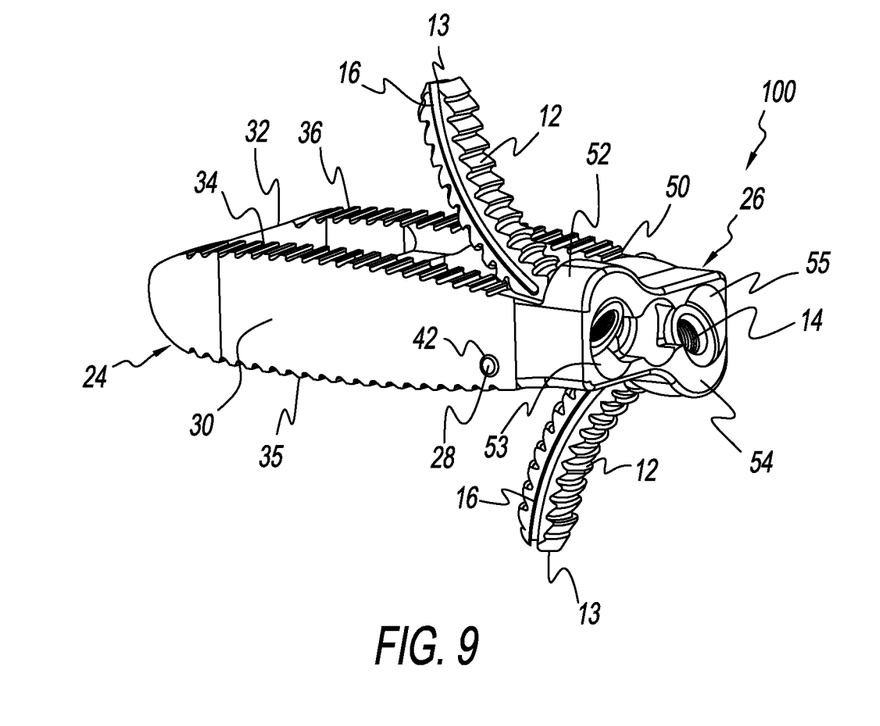
FIG. 9 is a an end side isometric view of the assembled cage and endplate with two flexible bards received in the endplate.
Figure 10:
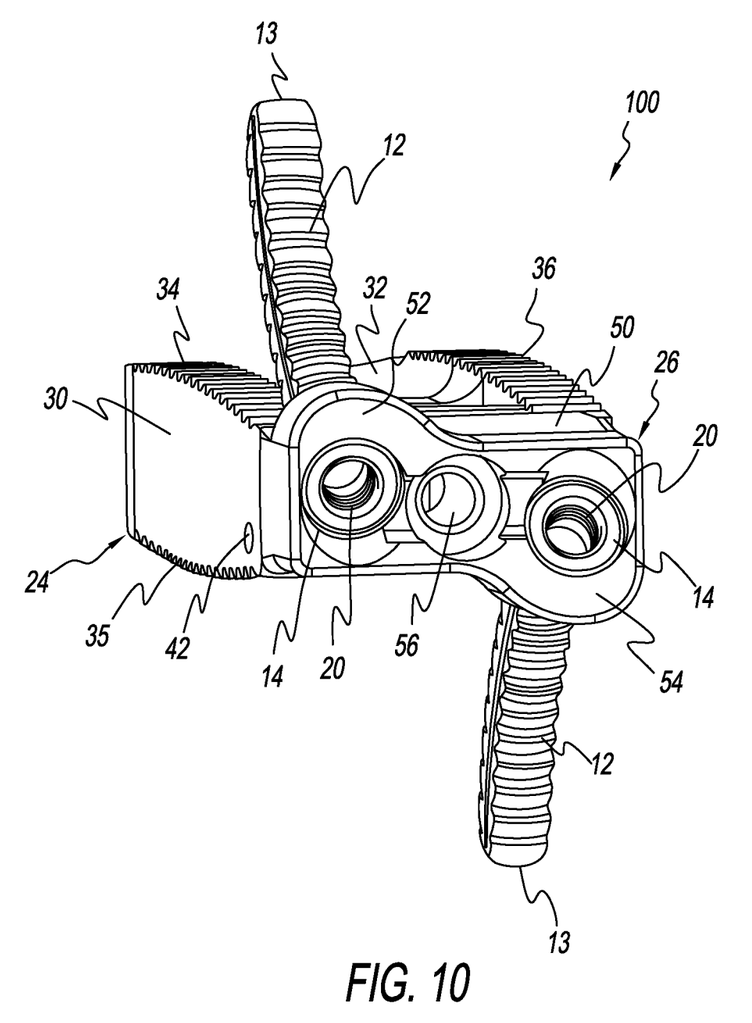
FIG. 10 is an isometric end view of the assembled interbody cage implant of FIG. 9.

The endplate 25 is defined by a body 26 having a generally rectangular cuboid shape. The body 25 has a first boss 52 on a first side of the front (proximal) side thereof, the first boss 52 having a first bore 53 that extends from the front to a rear (distal) side of the body 26. The first bore 53 projects generally upward from the front to the rear side of the body. As best seen in FIG. 5, rearward of the first bore 53 is a surface 57 that slants upwardly. The first bore 53 and surface 57 cooperate to bend a flexible barb 10 upwardly when inserted into and through the first bore 53 (see FIGS. 8-10). The body 25 has a second boss 54 on a second side of the front (proximal) side thereof, the second boss 54 having a second bore 55 that extends from the front to a rear (distal) side of the body 26. The second bore 55 projects generally downward from the front to the rear side of the body. While not seen in the figures, rearward of the second bore 55 is a surface that slants downwardly (in like manner to the slanted surface 57 but in the opposite direction). The second bore 55 and surface cooperate to bend a flexible barb 10 downwardly when inserted into and through the first bore 53 (see FIGS. 9-10). It should be appreciated that the nomenclature first and second is arbitrary. Moreover, the slant of the first and second bores (and rearward slanting surface) may be reversed, or the body 26 itself may be reversed to that which is shown in the figures. Additionally, the endplate 25 may have more bores that slant a flexible barb into other or the same directions. As best seen in FIG. 10, the endplate 25 also has a central bore 56 that accepts an insertion tool (not shown).

The rear or distal portion of the body 26 has serrations, teeth or the like 50 on an upper (superior) surface thereof that provide gripping against the lower (inferior) surface of the upper vertebra, and serrations, teeth or the like 51 on a lower (inferior) surface thereof that provide gripping against the upper (superior) surface of the lower vertebra when implanted. The rear or distal portion of the body 26 also is configured for reception by and/or on the first and second legs 30, 31. Particularly, and as best seen in FIG. 5, a first rear side of the body 26 has a slanted surface 58 that corresponds in angle to the slant 46 of the end 40 of the first leg 30. A ridge 59 projects from the slanted surface 58 that is configured for reception in the slot (not seen) in the slant 46 of the end 40. A bore 62 is also provided in the slanted surface 58 below the ridge 59 that aligns with the bore 42 of the first leg 30. The bore 62 is sized to receive a pin 28. A second rear side of the body 26 has a slanted surface 60 that corresponds in angle to the slant 44 of the end 41 of the second leg 31. A ridge 61 projects from the slanted surface 60 that is configured for reception in the slot 45 in the slant 44 of the end 41. A bore 63 is also provided in the slanted surface 60 above the ridge 61 that aligns with the bore 43 of the second leg 31. The bore 63 is sized to receive a pin 28. Again, the nomenclature first and second is arbitrary.

Figure 6:
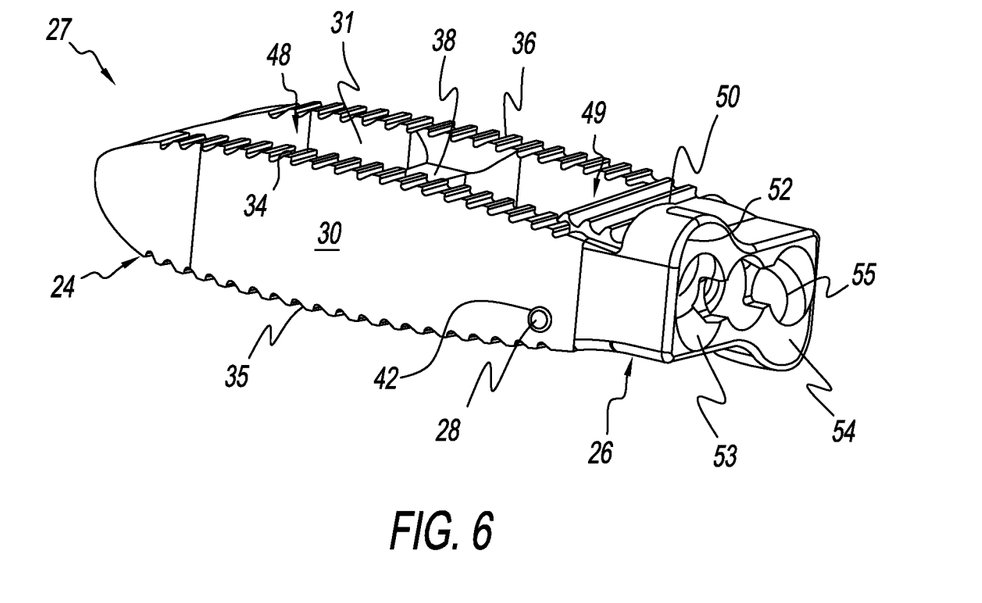
FIG. 6 is an isometric end side view of the assembled cage and endplate of the present interbody cage implant.
Figure 7:
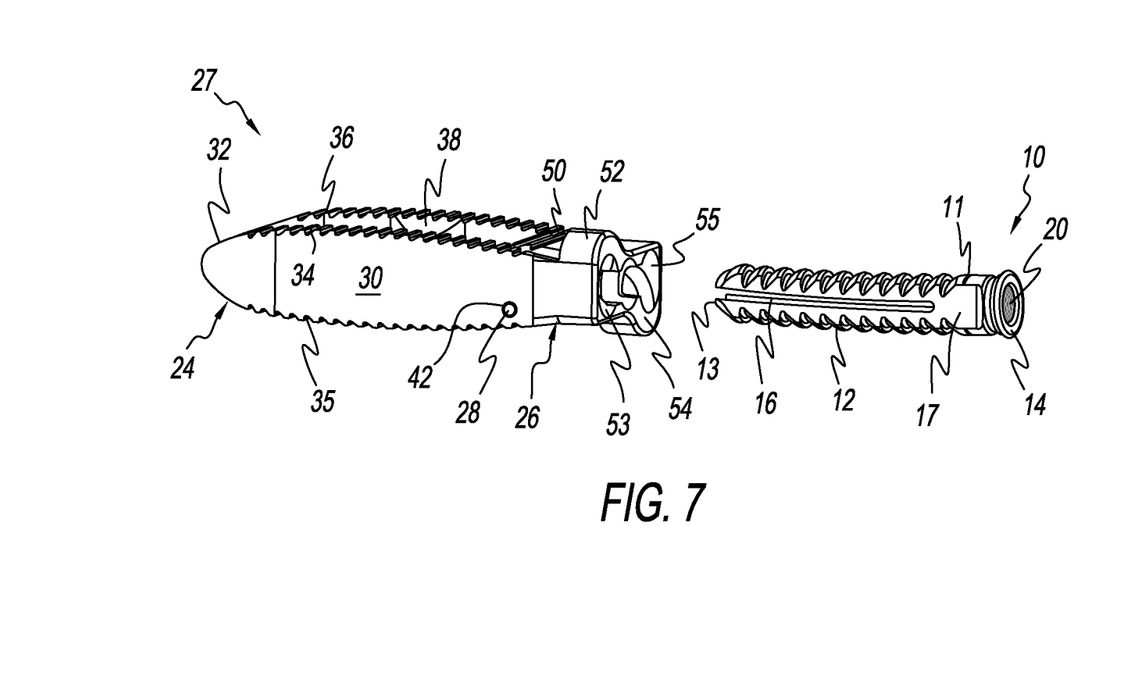
FIG. 7 is an isometric exploded side view of the assembled cage and endplate along with a flexible barb.
Figure 8:
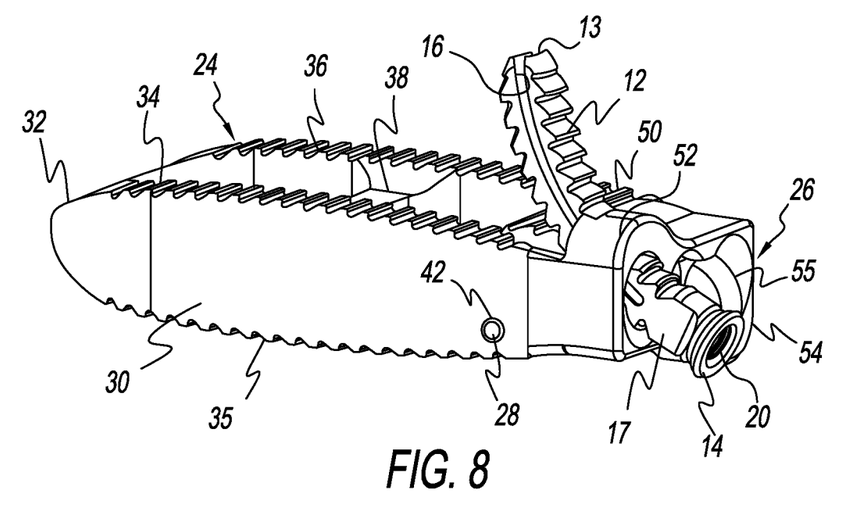
FIG. 8 is an end side isometric view of the assembled cage and endplate with a flexible barb received in the endplate.

FIG. 6 shows the cage assembly 27—i.e. the endplate received onto the cage, with pins installed. With the endplate received onto the legs, a second cavity 49 is defined between the transverse spur 38 and the rear of the endplate. FIG. 7 shows the cage assembly 27 with a flexible barb 10 ready for insertion into the first bore 53 of the endplate. FIG. 8 shows the flexible barb 10 received in the first bore of the endplate and bent or flexed upwardly (in the superior direction) by the configuration of the endplate as described above. FIGS. 9 and 10 show an assembled interbody cage implant 100 with a flexible barb 10 received in the first and second bores of the endplate, with the flexible barb 10 of the first bore bent or flexed upwardly (in the superior direction) by the configuration of the endplate and the flexible barb 10 of the second bore bent or flexed downwardly (in the inferior direction) by the configuration of the endplate as described above.

It should be appreciated that dimensions of the components, structures, and/or features of the present interbody cage implant may be altered as desired within the scope of the present disclosure.

What is claimed is:

1. A spinal implant comprising:
   an interbody cage;
   an endplate defining an upper surface, a lower surface, a front face, and a rear face; and
   a plurality of attachment barbs, each attachment barb having a flexible tubular body, the flexible tubular body defining a longitudinal axis and having a head on a proximal end and a tip on a distal end, first teeth situated on a first longitudinal surface of the flexible tubular body, and second teeth situated on a second longitudinal surface of the flexible tubular body, the flexible tubular body having a first configuration and a second arcuate configuration, the first configuration being different from the second arcuate configuration;
   the interbody cage having a body defining a first cavity, a first leg extending from the body and having a first end, and a second leg extending from the body and having a second end, the first and second legs defining an opening;
   the endplate attachable to the first end of the first leg and to the second end of the second leg wherein a second cavity is defined by the opening and the rear face of the endplate, the endplate having a first bore extending from a first side of the front face to a first upper side of the rear face, a second bore extending from a second side of the front face to a first lower side of the rear face, wherein the first bore is configured to retain the head of a first received attachment barb and manipulate the flexible tubular body of the first received attachment barb from the first configuration to the second arcuate configuration so as to bend the flexible tubular body of the first received attachment barb up and away from the first upper side of the rear face of the endplate for reception in an upper vertebral body, such that a portion of bent flexible tubular body of the first received attachment barb in the second arcuate configuration is positioned outside of the endplate, and wherein the second bore is configured to retain the head of a second received attachment barb and manipulate the flexible tubular body of the second received attachment barb from the first configuration to the second arcuate configuration so as to bend the flexible tubular body of the second received attachment barb down and away from the first lower side of the rear face of the endplate for reception in a lower vertebral body; such that a portion of bent flexible tubular body of the second received attachment barb in the second arcuate configuration is positioned outside of the endplate, and the first end of the first leg of the interbody cage and the second end of the second leg of the interbody cage each comprising a taper, and the rear face of the endplate comprising a pair of complementary tabs, with the taper of the first end of the first leg of the interbody cage and the taper of the second end of the second leg of the interbody cage each configured to receive one of the pair of complementary tabs of the rear face of the endplate.

2. The spinal implant of claim 1, wherein:
   the first leg of the interbody cage has an upper surface and a lower surface, anti-backout formations on the upper surface, and anti-backout formations on the lower surface; and
   the second leg of the interbody cage has an upper surface and a lower surface, anti-backout formations on the upper surface, and anti-backout formations on the lower surface.

3. The spinal implant of claim 1, wherein each flexible tubular body of each attachment barb has a first slit extending from the tip toward the head along a first flat, and a second slit extending from the tip toward the head along a second flat, the first and second flats disposed opposite one another on an exterior of the flexible tubular body and extending from the tip to the head.

4. The spinal implant of claim 3, wherein the head of each attachment barb has a threaded socket.

5. The spinal implant of claim 1, wherein:
   the first leg has a first lateral bore extending through and between a first lateral side and a second lateral side of the first leg;
   the second leg has a second lateral bore extending through and between a third lateral side and a fourth lateral side of the second leg;
   the endplate has a first reception bore in a first lateral side of the endplate, and a second reception bore in a second lateral side of the endplate; and
   a first attachment pin is receivable in and between the first lateral bore and the first reception bore, and a second attachment pin is receivable in and between the second lateral bore and the second reception bore.

6. The spinal implant of claim 5, wherein the endplate comprises a central bore extending between the front face of the endplate and the rear face of the endplate, the central bore providing communication with the second cavity.

7. The spinal implant of claim 6, wherein the endplate further has an anti-backout formation on the upper surface thereof, and an anti-backout formation on the lower surface thereof.

8. The spinal implant of claim 1, wherein the endplate further comprises a first boss and a second boss, with the first boss configured about the first bore and the second boss configured about the second bore.

9. The spinal implant of claim 1, wherein the attachment barbs further comprise a longitudinal bore, the longitudinal bore extending from the tip of the attachment barbs to the head of the attachment barbs.

10. The spinal implant of claim 1, wherein the first and second longitudinal surfaces are substantially linear in the first configuration and wherein the first and second longitudinal surfaces are arcuate in the second arcuate configuration.

11. The spinal implant of claim 1, wherein each attachment barb is an integral component formed of a flexible material.

12. A spinal implant comprising:
    an interbody cage;
    an endplate defining an upper surface, a lower surface, a front face, and a rear face; and attachment barbs, each attachment barb having a flexible tubular body defining a longitudinal axis with a head on a proximal end of the flexible tubular body, the flexible tubular body comprising:
a longitudinal bore configured concentrically about the longitudinal axis,
first teeth situated on a first portion of a first longitudinal surface of the flexible tubular body, and
second teeth situated on a second portion of a second longitudinal surface of the flexible tubular body,
wherein at least the first portion of the first longitudinal surface and the second portion of the second longitudinal surface are configurable in a first configuration and a second arcuate configuration, the first configuration being different from the second arcuate configuration;
the interbody cage having a body defining a first cavity, a first leg extending from the body and having a first end, and a second leg extending from the body and having a second end, the first and second legs defining an opening;
the endplate attachable to the first end of the first leg and to the second end of the second leg wherein a second cavity is defined by the opening and the rear face of the endplate, the endplate having a first bore extending from a first side of the front face to a first upper side of the rear face, a second bore extending from a second side of the front face to a first lower side of the rear face, wherein the first bore is configured to retain the head of a first received attachment barb and manipulate the flexible tubular body of the first received attachment barb from the first configuration to the second arcuate configuration upon insertion into the first bore so as to bend the flexible tubular body of the first received attachment barb up and away from the first upper side of the rear face of the endplate for reception in an upper vertebral body, such that a portion of bent flexible tubular body of the first received attachment barb is positioned outside of the endplate, and wherein the second bore is configured to retain the head of a second received attachment barb and manipulate the flexible tubular body of the second received attachment barb from the first configuration to the second arcuate configuration upon insertion into the second bore so as to bend the flexible tubular body of the second received attachment barb down and away from the first lower side of the rear face of the endplate for reception in a lower vertebral body, such that a portion of bent flexible tubular body of the second received attachment barb is positioned outside of the endplate; and
the first end of the first leg of the interbody cage and the second end of the second leg of the interbody cage each comprising a taper, and the rear face of the endplate comprising a pair of complementary tabs, with the taper of the first end of the first leg of the interbody cage and the taper of the second end of the second leg of the interbody cage each configured to receive one of the pair of complementary tabs of the rear face of the endplate.

13. A spinal interbody implant comprising:
a spine cage;
an endplate defining an upper surface, a lower surface, a front face, and a rear face; and
attachment barbs, each attachment barb having a flexible tubular body and a head on a proximal end thereof, a tip on a distal end thereof, first serrations situated on a first longitudinal surface of the flexible tubular body, and second serrations situated on a second longitudinal surface of the flexible tubular body, the flexible tubular body defining a longitudinal axis and having a first configuration and a second arcuate configuration, the first configuration being different from the second arcuate configuration;
the spine cage having a body, a first leg extending from the body and having a first end, and a second leg extending from the body and having a second end, the first and second legs defining an opening;
the endplate attachable to the first end of the first leg and to the second end of the second leg, the endplate having a first bore extending from a first side of the front face to a first upper side of the rear face, and a second bore extending from a second side of the front face to a first lower side of the rear face, and a central bore located between the first bore and the second bore, wherein the first bore is configured to retain the head of a first received attachment barb and manipulate the first received attachment barb from the first configuration to the second arcuate configuration so as to bend the first received attachment barb to direct the tip up and away from the first upper side of the rear face of the endplate for reception in an upper vertebral body, such that a bent portion of the first received attachment barb in the second arcuate configuration is positioned outside of the endplate, and wherein the second bore is configured to retain the head of a second received attachment barb and manipulate the second received attachment barb from the first configuration to the second arcuate configuration so as to bend the second received attachment barb to direct the tip down and away from the first lower side of the rear face of the endplate for reception in a lower vertebral body, such that a bent portion of the second received attachment barb in the second arcuate configuration is positioned outside of the endplate;
the first end of the first leg of the spine cage and the second end of the second leg of the spine cage each comprise an angled taper and a slot, wherein the angled taper is planar and angled away from a central cavity of the spine cage;
and the rear face of the endplate comprising a pair of complementary tapers each comprising a complementary ridge, each of the ridges configured to be received by a respective one of the slots, and each of the pair of complementary tapers configured to be received by a respective one of the angled tapers.

14. The spinal interbody implant of claim 13, wherein:
the first leg of the spine cage has an upper surface and a lower surface, anti-backout formations on the upper surface, and anti-backout formations on the lower surface; and
the second leg of the spine cage has an upper surface and a lower surface, anti-backout formations on the upper surface, and anti-backout formations on the lower surface.

15. The spinal interbody implant of claim 14, wherein:
one of the ridges comprises a first attachment formation on a first lateral side of the endplate, and the other of the ridges comprises a second attachment formation on a second lateral side of the endplate;
the slot on the first end of the first leg of the spine cage comprises a first attachment reception formation, and the slot on the second end of the second leg of the spine cage comprises a second attachment reception formation;

the first attachment formation of the endplate is received in the first attachment reception formation of the first leg; and the second attachment formation of the endplate is received in the second attachment reception formation of the second leg.

16. The spinal interbody implant of claim 15, wherein:

the first leg has a first lateral bore extending through and between a first lateral side and a second lateral side of the first leg;

the second leg has a second lateral bore extending through and between a third lateral side and a fourth lateral side of the second leg;

the endplate has a first reception bore in the first lateral side of the endplate, and a second reception bore in the second lateral side of the endplate; and a first attachment pin is receivable in and between the first lateral bore and the first reception bore, and a second attachment pin is receivable in and between the second lateral bore and the second reception bore.

17. The spinal interbody implant of claim 16, wherein the central bore extends between the front face of the endplate and the rear face of the endplate, the central bore providing communication with a cavity defined by the opening and the rear face of the endplate.

18. The spinal interbody implant of claim 17, wherein the endplate further has an anti-backout formation on the upper surface thereof, and an anti-backout formation on the lower surface thereof.

19. The spinal interbody implant of claim 13, wherein each flexible tubular body of each attachment barb has a first slit extending from the tip toward the head along a first flat, and a second slit extending from the tip toward the head along a second flat, the first and second flats disposed opposite one another on an exterior of the flexible tubular body extending from the tip to the head.

20. The spinal interbody implant of claim 19, wherein the head of each attachment barb has a threaded socket.

21. The spinal interbody implant of claim 13, wherein the attachment barbs further comprise a longitudinal bore, the longitudinal bore extending from the tip of the attachment barbs to the head of the attachment barbs.

\* \* \* \* \*